United States Patent [19]

Etzweiler et al.

[11] Patent Number: 5,525,589
[45] Date of Patent: Jun. 11, 1996

[54] CYCLIC COMPOUNDS

[75] Inventors: Franz Etzweiler, Greifensee; Daniel Helmlinger, Dübendorf, both of Switzerland

[73] Assignee: Givaudan-Roure Corporation, Clifton, N.J.

[21] Appl. No.: 198,339

[22] Filed: Feb. 18, 1994

[30] Foreign Application Priority Data

Feb. 24, 1993 [CH] Switzerland .................. 567/93

[51] Int. Cl.⁶ .................................................. A61K 7/46
[52] U.S. Cl. ...................... 512/23; 512/24; 512/6; 512/9; 512/22
[58] Field of Search ................................. 512/23

[56] References Cited

U.S. PATENT DOCUMENTS

| | | | |
|---|---|---|---|
| 2,840,599 | 6/1958 | Somerville et al. | 512/23 |
| 4,375,428 | 3/1983 | Helmlinger et al. | 512/23 |
| 4,617,145 | 10/1986 | Schreiber et al. | 512/23 |
| 4,757,051 | 7/1988 | Gramlich et al. | 512/23 |
| 4,888,323 | 12/1989 | Matsuda et al. | 512/23 |

FOREIGN PATENT DOCUMENTS

| | | |
|---|---|---|
| 1789 | 1/1987 | Japan. |
| 131405 | 5/1990 | Japan. |

OTHER PUBLICATIONS

Abstract, JP 131 405/1990 (May 1990).
Abstract, JP 1789/1987 (Jan. 1987).
Chemical Abstracts 61–06929E (May 1977).
Chemical Abstracts 68–086692 (Mar. 1968).
Chemical Abstracts 68–064387 (1968).
Chemical Abstracts 83–096905 (1975).
Chemical Abstracts 79–136579 (1973).
Chemical Abstracts 64–01979B (1960).
Chemical Abstracts 64–01978H (1966).
Arctander, S., "Perfume and Flavor Chemicals," (1969), references 437 and 438.

*Primary Examiner*—James H. Reamer
*Attorney, Agent, or Firm*—George M. Gould; George W. Johnston; Mark E. Waddell

[57] ABSTRACT

The present invention is concerned with novel odorant compositions which are characterized by a content of cyclic compounds of the formula

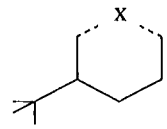

I wherein ... X ... has one of the meanings a)

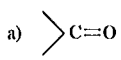

b)

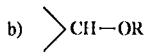

wherein R is H, $COCH_3$, $COCH_2CH_3$, $CO-CH(CH_3)_2$, $CO-CH=CH_2$, $COOCH_3$
whereby the cis/trans ratio in the isomers of I is 65–95:35–5;

c)

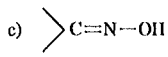

d)

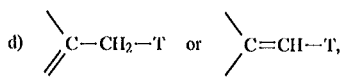

whereby T = CN or CHO e)

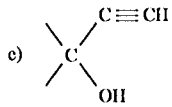

f) 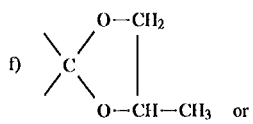 or g)

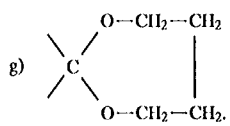

From this group of compounds the compounds I' with the meanings b), d), f) and g) are novel compounds.

1 Claim, No Drawings

CYCLIC COMPOUNDS

BACKGROUND OF THE INVENTION

The present invention is concerned with novel odorant compositions.

DETAILED DESCRIPTION

The present application describes odorant compositions having 1) an effective amount of a cyclic compound of the formula;

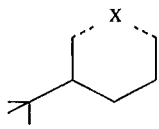

wherein ... X ... is a) 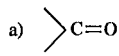 C=O b) 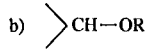 CH—OR wherein R is H, COCH$_3$, COCH$_2$CH$_3$, CO—CH(CH$_3$)$_2$, CO—CH=CH$_2$, COOCH$_3$
whereby the cis/trans ratio in the isomers of I is about 65-95:35-5;

c) 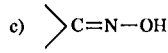 C=N—OH d) 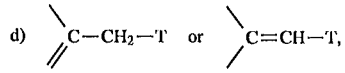

whereby T is CN or CHO e) 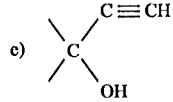

f) 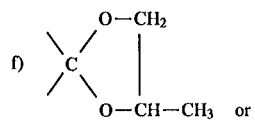 or g) 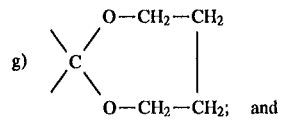 and 2) another olfactory agent.

From this group of compounds, with the meanings for X of b), d), f) and g) are novel compounds. These novel compounds are also designated as compounds of formula I'. The remaining compounds of formula I (Ia, Ic and Ie) and processes for their production are to some extent known, but their organoleptic properties and use in odorant compositions have not been described or suggested. As used herein, compounds of formula I wherein X has the specific meanings a) through g) described above, shall be designated compounds of formula I a) through I g), respectively.

Accordingly, the invention is also concerned with the novel compounds I', their manufacture, odorant compositions which contain compounds I or I' as organoleptic active substances as well as the use of the compounds I as odorants.

Formula I and I' also embrace the possible isomers. Thus in the case of compounds Ib) c) and e), the cis/trans isomers are also embraced. In the case of compounds Id) the double bond isomers, and in the case of compounds If) the diastereomers are embraced.

The process for the manufacture of the novel compounds I' in accordance with the invention comprises a) catalytically hydrogenating known 3-tert.butyl-phenol using Raney-nickel as the catalyst to the alcohol I'b and optionally correspondingly esterifying the thus-obtained 3-tert.butyl-cyclohexanol to form compounds Ib', or b) derivatizing known 3-tert.butyl-cyclohexanone (I'a) to a compound I' with X=d), f) or g).

The manufacture of all of these derivatives proceeds without exception in a manner known per se, with the suitable parameters being the following:

Derivatives I'b

α)
Hydrogenation of a phenol with Raney-nickel in a manner known per se

Temperature range: about 100° to about 170° C., preferably about 150° C.

Pressure range: about 10 to 50 bar, especially about 20 bar (H$_2$)

Solvent: optional, e.g. CH$_3$COOH, C$_2$H$_5$OH etc.

α) Manufacture of the esters from the alcohols obtained according to procedure α)

β1) Heating the cyclic alcohol I' with the corresponding acid to the reflux temperature of benzene, toluene, etc., conveniently on a water separator; the presence of an acid catalyst such as a mineral acid or an organic acid, e.g. sulphuric acid, phosphoric acid, p-toluenesulphonic acid, etc., is necessary.

β2) Analogous reaction of the alcohol I' in the same solvent as β1) with in place of the acid an acid derivative such as anhydride or halide in the presence of a base, preferably an organic base such as a secondary or tertiary amine, e.g. pyridine, piperidine, etc.

Derivatives Ic

The manufacture of the oximes (Ic) proceeds conveniently in an entirely conventional manner starting from known compound Ia, thus e.g. using a hydroxylamine hydrohalide, e.g. the hydrochloride, conveniently in aqueous medium or in methanol, ethanol, etc. and in the presence of a base such as pyridine, sodium hydroxide, Na$_2$CO$_3$, etc.

Derivatives I' d)1 [T is CN]

Knoevenagel condensation of 3-tert.butylcyclohexanone (Ia) with cyanoacetic acid (a) or with acetonitrile (b)

(a) The catalyst is conveniently a weak base such as NH$_4$.O$_2$CCH$_3$, pyridine, piperidine, triethylamine, etc.
Solvent: e.g. methanol, benzene, toluene, etc.
Reaction temperature: preferably elevated, esp. the reflux temperature of the solvent.

(b) In this case the reaction is conveniently carried out in the presence of a strong base, for example an alkali hydroxide, e.g. KOH or NaOH.

Derivatives I'd)2, [T is CHO]

α) Treatment of 3-tert.butyloxycyclohexanone (Ia) with an acetylide (e.g. Li, Na or K acetylide, etc.) in DMF, another polar solvent or also in ammonia, etc.

β) Rearrangement of the known acetylenic alcohol Ie using catalysts based on silylvanadates. Tris(triphenylsilyl)vanadate is a preferred catalyst. The reaction is conveniently carried out in solvents such as benzene, toluene or xylene, etc. and conveniently at elevated temperatures, for example at the reflux temperatures of the solvents.

The derivatives f) and g) are accessible by usual ketalization of 3-tert.butylcyclohexanone (Ia) using 1,4-butanediol or 1,2-propanediol. The ketalization is carried out in a manner known per se, i.e. catalytically, conveniently using a strong acid such as p-toluenesulphonic acid and in solvents such as benzene or toluene. The reaction is conveniently carried out at elevated temperatures and while using a water separator.

The purification of the compounds I and I' can be effected in a s manner known per se, e.g. by recrystallization, distillation or by chromatography.

Having regard to their valuable olfactory properties with a very broad spectrum, compounds I are suitable as odorants, especially in combination with the extensive range of natural and synthetic odorants or olfactory agents which are nowadays available for the creation of perfume compositions which can be used in all spheres of application. Examples of the numerous known odorant ingredient of natural or synthetic origin, whereby the range of the natural raw substances can embrace not only readily volatile but also moderately volatile and difficultly volatile components and that of the synthetics can embrace representatives from several classes of substances, are:

Natural products, such as tree moss absolute, basil oil, tropical fruit oils (such as bergamot oil, mandarin oil, etc.), mastix absolute, myrtle oil, palmarosa oil, patchouli oil, petit grain oil, wormwood oil, lavender oil, rose oil, jasmine oil, ylang-ylang oil, sandalwood oil, alcohols, such as farnesol, geraniol, linalool, nerol, phenyl-ethyl alcohol, rhodinol, cinnamic alcohol, cis-3-hexenol, menthol, α-tocopherol, aldehydes, such as citral, α-hexylcinnamaldehyde, hydroxycitronellal, Lilial® (p-tert.butyl-α-methyl-dihydrocinnamaldehyde), methylnonylacetaldehyde, phenylacetaldehyde, anisaldehyde, vanillin, ketones, such as allylionone, α-ionone, β-ionone, isoraldein (isomethyl-α-ionone), verbenone, nootkaton, geranylacetone, esters, such as allyl phenoxyacetate, benzyl salicylate, cinnamyl propionate, citronelly acetate, decyl acetate, dimethylbenzylcarbinyl acetate, ethyl acetoacetate, ethyl acetylacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate, etc., lactones, such as γ-undecalactone, δ-decalactone, pentadecan-15-olid, various components often used in perfumery, such as indole, p-menthane-8-thiol-3-one, methyleugenol, eugenol, anethol.

The odorant compositions manufactured using compounds I, especially those having a flowery, aldehydic, agrestic, marinic (marine), amber-like, woody direction, are especially fascinating by virtue of their originality.

In their use as odorants the compounds of formula I (or their mixtures) can be employed in effective olefactory amounts within wide limits which in compositions can extent, for example, from about 0.1 (detergents) to about 30 weight percent (alcoholic solutions) without these values being, however, limiting values, since the experienced perfumer can also achieve effects with even lower concentrations or can synthesize novel complexes with even higher dosages. The preferred concentrations vary between about 0.5 and about 10 weight percent. The compositions manufactured with the compounds I can be used for all kinds of perfumed consumer goods (eau de Cologne, eau de toilette, extracts, lotions, creams, shampoos, soaps, salves, powders, toothpastes, mouth washes, deodorants, detergents, fabric conditioners, tobacco, etc.).

Compound I can accordingly be used in the manufacture of compositions and—as will be evident from the above compilation—a wide range of known odorants or odorant mixtures can be used. In the manufacture of such compositions the known odorants or odorant mixtures enumerated above can be used in a manner known to the perfumer, as follows e.g. from W. A. Poucher, Perfumes, Cosmetics and Soaps 2, 7th edition, Chapman and Hall, London, 1974.

By virtue of their superior olfactory properties the compounds of formula I are preferably used in luxury perfumery and in compositions for cosmetics.

Preferred compounds are the acetate, the ketone and the nitriles, see formula Ia, b and d, The following Examples illustrate the invention.

In these following Examples the cis/trans ratio was determined in each case by gas chromatography via the area ratio.

The same procedure was used to determine the double bond isomers (Examples 7, 8) and the diastereomers (Example 9).

EXAMPLE 1

300 g (2 mol) of 3-tert.butylphenol are placed in an autoclave. 30 g of Raney-nickel are added and the mixture is now hydrogenated at 20 bar of hydrogen and 160° C. for 4¾ hours while stirring. The reaction mixture is left to cool to room temperature, diluted with a small are out of ether, filtered over Celite and evaporated. In this manner there are obtained 299.9 g (96%) of a mixture of trans-3tert.butylcyclohexanol (23%) and cis-3-tert.butylcyclohexanol (77%).

Odor of the mixture: earthy, moss-like, woody, camphor-like, green-spicy.

Spectral data:
a) trans-3-tert. Butylcyclohexanol
H-NMR (CDCl$_3$, 200 MHz): 0.85, s, 9H, t-butyl; 4.14–4.215, broad multiplet, 1H, —CHOH); MS: 138(5); 123(16); 99(15); 83(25); 82(38); 81(40), 80(21); 67(33); 57(100); 56(36); 55(25); 41(45); 29(23);

b) cis-3-tert.Butylcyclohexanol
H-NMR (CDCl$_3$, 200 MHz): 0.86, s, 9H, t-butyl; 3.47–3.63, broad multiplet, 1H, CH—OH; MS: 123(13); 99(22); 83(25); 82(56); 81(33); 67(45); 57(100); 56(31); 55(28); 41(50); 29(25).

EXAMPLE 2

A mixture of 109.39 g (0.7 mol) of 3-tert.butylcyclohexanol (prepared according to Example 1), 46.24 g (0.77 mol) of acetic acid and 231 mg of p-toluenesulphonic acid, dissolved in 210 ml of toluene, is refluxed on a water separator for 6 hours. Then, the mixture is washed with water, extracted with ether, washed with a 10% bicarbonate solution and water, dried and evaporated. In this manner there are obtained 142 g of crude product. After distillation there are obtained 105 g (76%) of olfactorily satisfactory product which contains 19% trans-3-tert.butylcyclohexyl acetate and 78% cis-3tert.butylcyclohexyl acetate.

Odor of the mixture: woody, iris-like, fresh, flowery, slightly camphor-like.

Spectral data:

a) trans-3-tert.Butylcyclohexyl acetate

H-NMR (CDCl$_3$, 200 MHz): 0.84, s, 9H, t-butyl; 2.06, s, 3H, C$\underline{H}_3$—CO—O; 5.10–5.18, multiplet C$\underline{H}$—O—; MS: 141(17); 123(16); 83(15); 82(49); 81(40); 67(42); 61(14); 57(100); 43(39); 41 (21);

b) cis-3-tert. Butylcyclohexyl acetate H-NMR (CDCl$_3$, 200 MHz): 0.86, s, 9H, t-butyl; 2.03, s, 3H, C$\underline{H}_3$—CO—O; 4,60–4,78, broad multiplet C$\underline{H}$—O; MS: 142(2); 138(5); 123(21); 117(4); 95(3); 83(31); 82(84) 81(25) 80(35); 67(59); 61(27); 57(100); 43(48); 41(21); 29(5).

EXAMPLE 3

A) 15.63 g (0.1 mol) of 3-tert.butylcyclohexanol (prepared according to Example 1), 8.7 g (0.11 mol) of pyridine are dissolved in 30 ml of toluene and 10.18 g (0.11 mol) of propionyl chloride are added dropwise. The mixture is then heated to 50° C., stirred for 4 hours, poured into water, extracted with ether, washed with 2N hydrochloric acid, water, 10% sodium bicarbonate solution and water, dried over magnesium sulphate and evaporated. The crude product (21.76 g) is initially subjected to a first distillation. The product obtained (17.6 g) is chromatographed (Kieselgel 60 Merck, 0.04–0.063 mm 150 g 2% ether in hexane) and thereupon again distilled. B.p.: 60° C./1 m bar. In this manner there are obtained 16.04 g (75%) of a mixture of trans-3tert.butylcyclohexanol propionate (21%) and cis-3-tert.butylcyclohexanol propionate (78%).

Odor of the mixture: fruity, resembling grapefruit, aldehydic.

Spectral data:

a) trans-3-tert.Butylcyclohexanol propionate

H-NMR (CDCl$_3$, 200 MHz): 0.83, s, 9H, t-butyl; 5.12–5.19, multiplet C$\underline{H}$—O—; MS: 155(23); 138(5); 123(19); 95(3); 83(9); 82(42); 81(36); 80(29); 75(26); 67(27); 57(100); 41(11); 29(9);

b) cis-3-tert.Butylcyclohexanol propionate

H-NMR (CDCl$_3$, 200 MHz): 0.86, s, 9H, t-butyl; 4.62–4.78, broad multiplet C$\underline{H}$—O; MS: 138(7); 131(3); 123(16); 83(14); 82(58); 81(17); 80(29); 75(44); 67(42); 57(100); 41(16); 29(14).

B) 3-tert. Butylcyclohexylacrylate is also prepared analogously to the procedure described above under A) by treating 3-tert.butylcyclohexanol with acrylic acid chloride in toluene in the presence of pyridine.

Odor: fresh, green, fruity, tomato, plum.

Spectral data:

cis/trans 3-tert. Butylcyclohexyl acrylate mixture in the ratio 76/23 IR: 1725, 1618, 1630 cm$^{-1}$ MS: 153(4); 138(4); 123(14); 82(58); 73(26); 67(36); 57(100); 55(52); 41(24); 27(13).

EXAMPLE 4

A mixture of 15.63 g (0.1 mol) of 3-tert.butylcyclohexanol (prepared according to Example 1), 9.70 g (0.11 mol) of isobutyric acid and 100 mg of p-toluenesulphonic acid, dissolved in 100 ml of toluene, is refluxed on a water separator for 5 hours and 40 minutes. The mixture is then washed with water, extracted with ether, washed with saturated bicarbonate solution and water, dried and evaporated. In this manner there are obtained 22 g of crude product. This product is chromatographed (Kieselgel 60 Merck 150 g, 0.04–0.063 mm 180 g, eluent 2% ether in hexane) and thereupon distilled. In this manner there are obtained 13.2 g (58%) of a mixture of trans-3-tert.butylcyclohexanol isobutyrate (22%) and cis-3-tert.butylcyclohexanol isobutyrate (77%).

Odor of the mixture: fruity (apricot), woody, lactone-like, green, aldehydic, flowery.

Spectral data:

a) trans-3-tert.Butylcyclohexanol isobutyrate

H-NMR (CDCl$_3$, 200 MHz): 0.83, s, 9H, t-butyl; 1,18, dd, J=7, J=0.5; 2.43–2.64, multiplet, J=7 Hz, C$\underline{H}$(CH$_3$)$_2$; 5.10–5.1, multiplet C$\underline{H}$—O—; MS: 169(5); 138(5); 123(8); 89(33); 83(11); 82(26); 81(22); 80(23) 71(16); 67(19); 57(100); 56(7); 5(9); 43(26); 41(20);

b) cis-3-tert.Butylcyclohexanol isobutyrate

H-NMR (CDCl$_3$, 200 MHz): 0.86, s, 9H, t-butyl; 1.16, d, J=7 Hz; 2.38–2.60, multiplet, J=7 Hz, C$\underline{H}$(CH$_3$)$_2$; 4.60–4.76, broad multiplet C$\underline{H}$—O; MS: 145(2); 138(6); 123(11); 89(43); 83(15); 82(36); 81(14); 80(22); 71(15); 69(7); 67(24); 57(100); 43(28); 41(17).

EXAMPLE 5

15.63 g (0.1 mol) of 3-tert.butylcyclohexanol (prepared according to Example 1), 8.7 g (0.11 mol) of pyridine are dissolved in 30 ml of toluene and 10.4 g (0.11 mol) of methyl chloroformate are added dropwise. A slight exothermic reaction and the formation of a precipitate are observed. The mixture is heated to 50° C. while stirring for 5 hours and once more one equivalent of pyridine (7.9 g) and one equivalent of chloroformic acid (9.45 g) are added. After 22½ hours the mixture is treated with water, extracted with ether, washed with 2N hydrochloric acid, water, saturated bicarbonate solution and water, dried over magnesium sulphate and evaporated. The crude product (15.84 g) is chromatographed (Kieselgel 60 Merck, 0.04–0.063 mm) 150 g eluent (2% ether in hexane) and distilled. In this manner there are obtained 7.96 g (37%) of a mixture of trans-3-tert.butylcyclohexyl methyl carbonate (9%) and cis-3-tert.butylcyclohexyl methyl carbonate (81%).

Odor of the mixture: green, woody, flowery, fruity, spicy, earthy.

Spectral data:

a) trans-3-tert. Butylcyclohexyl methyl carbonate

H-NMR (CDCl$_3$, 200 MHz): 0.84, s, 9H, t-Butyl; 3.78, s, C$\underline{H}_3$—O: 4.98–5.07, multiplet CH—O—; MS: 157(14); 138(3); 123(17); 83(21); 82(50); 81(42); 80(21); 77(47); 67(47); 57(100); 41(27);

b) cis-3-tert.Butylcyclohexyl methyl carbonate

H-NMR (CDCl$_3$, 200 MHz): 0.86, s, 9H, t-butyl; 3.77, s, C$\underline{H}_3$—.O; 4.46–4.64, multiplet C$\underline{H}$—O; MS: 159(15); 133(3); 123(24); 83(27); 82(90); 81(24); 80(13); 77(85); 67(57); 57(100); 56(21); 55(14); 41(25).

EXAMPLE 6

300 g (2 mol) of 3-tert.butylphenol are hydrogenated in the presence of 3 g of palladium-on-active charcoal 5% and 3 g of anhydrous sodium carbonate at 0.15–0.3 bar hydrogen over-pressure and 115° C. In an autoclave for 21 hours. The mixture is then filtered over Celite. The Celite is washed with ether and the solution is evaporated. In this manner there are obtained 310.8 g of crude product, namely 1.5% trans-tert.butylcyclohexanol, 3.5% cis-tert.butylcyclohexanol, 86% 3-tert.butylcyclohexanone and 7.6% 3-tert.butylphenol. This product can be purified by distillation. There are obtained 232 g (75%) of 3-tert.butylcyclohexanone, b.p. 75°–76° C., 2 mbar (olfactorily acceptable, purity 94%) in addition to 11.3 g (3.6%) of impure material (purity 92%).

Odor: Camphor like, aromatic, green, earthy, woody, pine-like, fruity, minty.

Spectral data:

3-tert.Butylcyclohexanone

H-NMR (CDCl$_3$, 200 HHz): 0.90, s, tert.butyl; MS: 154(16); 139(3); 99(14); 98(81); 97(24); 83(24); 70(18) 69(29); 57(100); 55(33); 41(54); 29(14).

EXAMPLE 7

8.42 g (0.15 mol) of KOH are added to 24.63 g of acetonitrile and the mixture is heated to reflux temperature while stirring. A solution of 15.43 g (0.1 mol) of 3-tert.butylcyclohexanone in 6,16 g of acetonitrile is added dropwise. The mixture is heated at reflux for 2.5 hours while stirring, then poured into water, extracted with ether, washed with water, dried over magnesium sulphate and evaporated. The crude product (18.4 g) is chromatographed (Kieselgel 60 Merck, 0.04–0.063 mm, 150 g, elution: with 2% ether in hexane) and distilled. In this manner there are obtained 6.39 g (36%) of crude product. This product contains 4 isomers in the ratio 9/40/9/40.

According to the NMR spectrum the two main isomers consist of E-and Z-3-tert.butylcyclohexylideneacetonitrile d)12 and d)14 and the byproducts consist of (3-tert.butyl-cyclohex-1-enyl)-acetonitrile and (3-tert.butyl-cyclohex-6-enyl)-acetonitrile d) 11 and d) 13.

Odor of the mixture: spicy (cumin), green, earthy, aldehydic, reminiscent of anis, aromatic, leather-like.

Spectral data:

H-NMR (CDCl$_3$, 200 MHz): mixture d)1 0.880, s, tert.butyl d) 12 or d) 14; 0.92, s, tert.butyl d) 12 or d) 14; 0.881, s, tert.butyl d)11 or d)13; 0.882, s, tert.butyl d) 11 or d) 13; 5.03–5.07, multiplet, 1H, d)12 and d)14, C=C$\underline{H}$—CN; 5.75–5.82, broad singlet d)11 and d)13, C$\underline{H}$=C—CH$_2$—CN; MS d)11: 177(6); 162(3); 121(16); 106(4); 94(56); 79(29); 57(100); 41(30); 32( 12); 28(36); MS d)12: 177(17); 163(13); 162(85); 122(24); 121(83); 120(63); 106(18) 97(30); 96(12); 94(44); 93(48); 91(12); 81(21); 80(33); 79(29); 77(18); 57(100); 56(12); 55(47); 43(21); 41(75); MS d)13: 177(6); 162(2); 121(17); 106(8); 93(7); 81(16); 80(13); 79(16); 69(9); 57(100); 41(28); 28(2); MS d)14: 177(22); 162(48); 134(7); 122(12); 121(34); 120(27); 106(12); 97(37); 96(12); 94(18); 93(19); 84(10); 81(20); 80(15); 79(16) 77(10); 69(16); 57(100); 55(39); 43(16); 41(69); 39(15); 29(15).

EXAMPLE 8

A mixture of 15.43 g (0.1 mol) of 3-tert.butylcyclohexanone, 0.4 g of ammonium acetate and 50 ml of toluene is heated to reflux temperature on a water separator, then 7.32 g (86 mmol) of cyanoacetic acid and 1.2 g (20 mmol) of acetic acid are added in small portions. After 23 hours at reflux temperature the mixture is cooled, washed with water, diluted with ether, washed with saturated sodium bicarbonate solution, then with water and evaporated. The crude product (19.52 g) is distilled. In this manner there are obtained 10 g (56% yield) consisting mainly of the two main isomers d)11 and d)13 and traces of compounds d)12 and d)14 (d)11:57.3%, d)12: 1%, d)13: 39.3%, d)14: 1.7%).

EXAMPLE 9

15.43 g (0.1 mol) of 3-tert.butylcyclohexanone, 8.37 g (0.11 mol) of 1,2-propanediol and 100 mg of p-toluenesulphonic acid are dissolved in 100 ml of toluene and refluxed on a water separator. After 5 hours at reflux the mixture is cooled and washed with water, then extracted with ether. The organic phase is washed with a bicarbonate solution and water. In this manner there are obtained 21.93 g of a crude product which consists mainly of three isomers (isomer ratio about 2/1/1). The fourth possible isomer probably can not be separated under the conditions of the gas chromatography.

Odor: fruity, green, woody, flowery, anis-like, aromatic, camphor-like, tobacco-like.

Spectral data:

2-Methyl-7-tert.butyl-1,4-dioxaspiro[4,5]decane

H-NMR (mixture of the two isomers in the ratio 2/1; CDCl$_3$, 200 MHz): 0.84, s, 9H, tert.butyl; 1.26, d, J=6 Hz, 3H, C$\underline{H}_3$—CH—; 1.28, d, J=6 Hz, 3H, C$\underline{H}_3$—CH—; 3.38–3.50, multiplet, 1H; 3.9–4.10, multiplet, 1H; 4.11–4.32, multiplet, 1H; MS f)1: 156(11); 155(100); 114(13); 113(91); 111(9); 100(4); 97(28); 69(15); 57(10); 55(35); 41(16); MS f)2: 156(12); 155(100); 114(8); 113(66); 111(9); 97(33); 79(2); 69(15); 55(33); 41(20); MS f)3: 155(80); 113(100); 111(14); 97(39); 69(33); 57(33); 56(10); 55(93); 43(21); 42(16); 41(69); 39(11); 29(18); 27(11).

EXAMPLE 10

15.43 g (0.1 mol) of 3-tert.butylcyclohexanone, 9.91 g (0.11 mol) of 1,4-butanediol and 0.1 g of p-toluenesulphonic acid are refluxed in 100 ml of toluene on a water separator. After 18 hours the mixture is cooled, washed with water and extracted with ether. The organic phase is washed with 10% bicarbonate solution, then with water, dried over magnesium sulphate and evaporated. The crude s product (19.2 g) is chromatographed (Kieselgel Merck 60, 0.04–0.063 mm 150 g, elution with 1% ether in hexane) and distilled (b.p. 108° C./1 mbar). In this manner there are obtained 8.11 g (36%) of 9-tert.butyl-1,6-dioxaspiro[5,6]dodecane.

Odor: woody, flowery, aromatic, camphor-like, fruity, minty, earthy.

Spectral data:

H-NMR (CDCl$_3$, 200 MHz): 0.86, s, 9H, tert.butyl; 3.58–3.78, broad doublet, 4H, J=14 Hz; MS: 226(8); 170(23); 169(90); 139(35); 128(15); 127(79); 115(18); 98(22); 97(69); 73(12); 69(26); 57(24); 55(100); 43(19); 41(46); 28(24).

EXAMPLE 11

2.2 g of triphenylsilanol, 0.16 g of stearic acid and 0.12 ml of vanadium isopropylate are added to 8.11 g (45 mmol) of 3-tert.butyl-1-ethyne-cyclohexan-1-ol (cis, trans mixture) dissolved in 80 ml of xylene and the mixture is heated to reflux temperature for 10 hours. It is then left to stand for 12 hours. It is washed with 50 ml of saturated sodium bicarbonate solution, extracted with ether, washed with water, dried and evaporated. The crude product (13.4 g) contains 10% 3-tert.butyl-1-acetaldehyde-1-cyclohexene d)21 or d)22, 10% 3-tert.butyl-1-acetaldehyde-6-cyclohexene d)21 or d)22, 21.4% E- or Z-3-tert.butylcyclohexylideneacetaldehyde d)23 or d)24, 24.2% E- or Z-3-tert.butylcyclohexylideneacetaldehyde d)23 or d)24. Fractions D1, D2 and D3 are obtained after distillation:

D1:1 g 42% d)21, 27% d)22 D2/D3:4.34 g 28% d)21, 37% d)22, 20% d)23, 8% d)24.

B.p.: 48°–52°/0.045 Torr.

The product had apparently isomerized during the distillation:

Spectral data:

3-tert.Butyl-1-acetaldehyde-1-cyclohexene d)21 or d)22

3-tert.Butyl-1-acetaldehyde-6-cyclohexene d)21 or d)22

H-NMR (CDCl$_3$, 200 MHz): mixture d)21+d)22 0.87, 0.88, 9H, tert.butyl; 2.97–3.04, 2H, broad singlet, CH$_2$—CO; 5.57–5.65, 1H, broad singlet, CH=C; 9.59 (dd, J=3 Hz, J=3 Hz), 1H, OCH—; 9.61 (dd, J=3 Hz, J=3 Hz), 1H, OCH—; MS d)21: 180(1); 124(48); 95(19); 93(10); 81(15); 80(49); 79(34); 67(11); 57(100); 41(35); 29(14) MS d)22: 180(1); 124(46); 95(19); 93(7); 81(16); 80(39); 79(23) 67(11); 57(100); 41(32); 39(10); 29(13).

E-3-tert.Butylcyclohexylideneacetaldehyde d)23 or d)24
Z-3-tert.Butylcyclohexylideneacetaldehyde d)23 or d)24

H-NMR (CDCl$_3$, 200 MHz): d)23 or d)24 0.90, s. 9H, tert.butyl; 3.3–3.42, broad doublet, J=13, 1H; 5.84, d, J=9, CH=C; 10.0, d, J=9 Hz, OCH;

H-NMR (CDCl$_3$, 200 MHz): d)23 or d)24 0.92, s, 9H, tert.butyl; 3.4–3.52 broad doublet, J=13, 1H; 5.84, d, J=9, CH=C; 10.04, d J=9, OCH; MS d)23: 180(0,2); 165(2); 123(100); 105(8); 95(17); 81(16); 80(11); 79(15); 67(16); 57(33); 55(14); 43(14); 41(28); 39(9); 29(13); MS d)24: 180(34); 163(4); 137(7); 124(16); 123(65); 109(23); 96(17); 95(37); 93(13); 91(11); 81(32); 80(30); 79(27); 77(13); 67(27); 57(100); 55(35); 53(14); 43(25); 41(55); 39(18); 29(24).

EXAMPLE 12

Odorant compositions

In Examples a) to n) the respective component placed in the first position and in brackets relates to the reaction product of the corresponding working Example, set forth above.

a) Perfume base, suitable for soap, flowery type

|  | Parts by weight |
|---|---|
| (2) | 30.00 |
| Benzyl acetate | 150.00 |
| Linalyl acetate | 40.00 |
| Phenylethyl alcohol | 50.00 |
| n-Decylaldehyde | 4.00 |
| Undecylenaldehyde | 5.00 |
| Lauric aldehyde | 5.00 |
| Ciste absolute | 1.00 |
| Coumarin | 70.00 |
| Dipropylene glycol | 261.00 |
| Estragol (n-allylanisole) | 1.00 |
| Ethyl-vanillin 10%/DIP | 5.00 |
| Geraniol intermediate 60 (3,7-dimethyl-octa-2,6-dienol) | 10.00 |
| Clove essence | 15.00 |
| Indolen (8,8-di-(1H-indol-1-yl)-2,6-dimethyl-octan-2-ol) | 1.00 |
| Ionanthem 100% (α-ionone) | 20.00 |
| Isoeugenol | 10.00 |
| Isoraldein 70 (methylionone) | 65.00 |
| Lilial | 30.00 |
| Linalool | 45.00 |
| Musk xylene | 25.00 |
| Orange cryst. [1-(2-naphthanenyl)ethanone] | 2.00 |
| Petitgrain ess. Paraguay | 5.00 |
| Styrax | 15.00 |
| α-Terpinol | 30.00 |
| Vetiver ess. Java | 25.00 |
| Ylang ylang ess. | 80.00 |
| Total: | 1000.00 |

In the above composition the compound I intensifies the woody and iris notes and confers strength to the flowery composition.

b) Masculine eau de toilette, woody to amber-like type

|  | Parts by weight |
|---|---|
| (2) | 30.00 |
| Ambrettolid | 2.00 |
| Ambroxan [3aR-(3aα,5aβ,9aα,9bβ)-dodecahydro-3a,6,6a,9a-tetramethyl-naphtho[2,1-B]furan] | 2.00 |
| Bergamot ess. | 200.00 |
| Cedryl methyl ether | 80.00 |
| Citric ess. | 60.00 |
| Citronellol extra | 40.00 |
| Civette absolute | 1.00 |
| Coumarin | 15.00 |
| Cyclohexal | 70.00 |
| Dipropylene glycol | 20.00 |
| Hedion | 200.00 |
| Isoraldein 70 | 50.00 |
| Lavandin | 60.00 |
| Methyl cedryl ketone | 50.00 |
| Patchouli ess. | 100.00 |
| Sandalore | 15.00 |
| Vanillin | 5.00 |
| Total: | 1000.00 |

In this composition the compound I (of woody and amber-like character) confers harmony, it accentuates the fresh aspect and the impact.

c) Perfume base for shampoos of a flowery, aldehydic type

|  | Parts by weight |
|---|---|
| (2) | 40.00 |
| Hexylcinnamaldehyde | 350.00 |
| Lauric aldehyde 10%/DIP | 5.00 |
| Aldehyde iso C$_{11}$ (10%/DIP) (mixture of 10-undecenal and cis,trans 9-undecenal) | 5.00 |
| Citronellol | 60.00 |
| Coumarin | 35.00 |
| β-Dihydro-ionone | 10.00 |
| Dipropylene glycol | 40.00 |
| Ebanol (3-methyl-5-(2,2,3-trimethyl-3-cyclo-pent-1-yl)-4-penten-2-ol) | 1.00 |
| Fixolid | 100.00 |
| Gardenol (methylphenylcarbinyl acetate) | 7.00 |
| Geraniol intermediate 60 | 60.00 |
| Givescone | 2.00 |
| Heliotropin | 20.00 |
| Iso E super | 25.00 |
| Isoraldein 40 | 70.00 |
| Lilial | 100.00 |
| Methyl cedryl ketone | 40.00 |
| Ylang ylang ess. | 30.00 |
| Total: | 1000.00 |

In the above composition the compound I binds the flowery, green, aldehydic top notes with the woodynotes and confers the required volume to the composition.

d) Multipurpose base for agrestic perfume type, sea, chypre

|  | Parts by weight |
|---|---|
| (8) | 30.00 |
| Methylnonylaldehyde | 10.00 |
| Aldehyde mandarin (dodec-2-en-1-al) | 10.00 |
| Armoise ess. | 15.00 |
| Calone (7-methyl-3,4-dihydro-2H-1,5-benzodioxepin-3-one) | 5.00 |
| Cashmeran (1,2,3,5,6,7-hexahydro-1,1,2,3,3-pentamethyl-4H-inden-4-one) | 5.00 |
| Clonal (dodecanitrile) | 30.00 |
| Coumarin | 5.00 |
| Dipropylene glycol | 370.00 |
| Evernyl (2,4-dihydroxy-3,6-dimethyl-benzoic acid methyl ester) | 20.00 |
| Florhydral (3-(3-isopropylphenyl)-butanal) | 10.00 |

| | Parts by weight |
|---|---|
| Hedion | 55.00 |
| Homofuronol 20%/PG | 1.00 |
| Isobutyl-quinoline (2-(2-methylpropyl)quinoline | 2.00 |
| Methyl 2-nonynoate | 1.00 |
| Rose oxide 10% in Carbitol (tetrahydro-4-methyl-2-(2-methyl-1-propenyl)-2H-pyran) | 10.00 |
| Benzyl salicylate | 170.00 |
| Tagetes ess. | 1.00 |
| Thyme essence | 5.00 |
| Tropional (α-methyl-1,3-benzodioxole-5-propanal) | 100.00 |
| Undecatriene | 10.00 |
| Total: | 1000.00 |

The compound I furnishes the typical leather-like tonality and intensifies the modern sea character.

e) Perfume for soap

| | Parts by weight |
|---|---|
| (7) | 5.00 |
| Benzyl acetate | 40.00 |
| Dimethylbenzylcarbinol acetate | 10.00 |
| Phenylethyl alcohol | 120.00 |
| Hexylcinnamaldehyde | 100.00 |
| Undecylenaldehyde | 3.00 |
| Butylhydroxytoluene | 2.00 |
| Citrus ess. reconstitution | 70.00 |
| Citronellol | 80.00 |
| Coumarin | 20.00 |
| γ-Decalactone | 3.00 |
| Dihydromyrcenol | 40.00 |
| Eugenol | 10.00 |
| Fixolid | 50.00 |
| Gardenol | 10.00 |
| Hedion | 50.00 |
| Isoraldein 70 | 80.00 |
| Lilial | 40.00 |
| Linalol | 30.00 |
| Methyl cedryl ketone | 60.00 |
| Benzyl salicylate | 147.00 |
| Ylang ylang ess. | 30.00 |
| Total: | 1000.00 |

The composition receives an impact and freshness by the presence of I, brought about by its strength, green rooty odor and woody and vetiver character.

f) Masculine eau de toilette, of a fresh, woody, amber-like type

| | Parts by weight |
|---|---|
| (5) | 30.00 |
| Linalyl acetate | 20.00 |
| Bergamot ess. | 100.00 |
| Sandalwood essence | 30.00 |
| Coumarin | 3.00 |
| Cyclal C (3,5-dimethyl-cyclohex-3-ene-1-carboxaldehyde) | 1.00 |
| Cyclohexal (4-(4-hydroxy-4-methyl-pentyl)cyclohex-3-ene-1-carboxaldehyde) | 60.00 |
| Dihydro-myrcenol | 20.00 |
| Dipropylene glycol | 232.00 |
| Evernyl | 3.00 |
| Fixolid | 140.00 |
| Hedion | 20.00 |
| Indole 10%/DIP | 3.00 |
| β-Ionone | 5.00 |
| Iso E super (1-(1,2,3,4,5,6,7,8-octahydro-2,3,8,8-tetramethyl-2-naphthenyl)-ethanone) | 220.00 |
| Isobutylquinoline | 2.00 |
| Methyl cedryl ketone | 100.00 |
| Methyl octynecarbonate | 8.00 |
| Patchouli ess. | 10.00 |
| Vanillin 10% DIP | 3.00 |
| Total: | 1000.00 |

By the compound I the composition receives all of the character of the woody and amber-like notes, the impressive accord is due for the most part to the strength and the volume of I.

g) Perfume for soap

| | Parts by weight |
|---|---|
| Oxime I'c) | 10.00 |
| Bornyl acetat | 70.00 |
| Vetivenyl acetate | 200.00 |
| Bergamot ess. | 100.00 |
| Citrus ess. | 100.00 |
| Dihydromyrcenol | 50.00 |
| Dipropylene glycol | 205.00 |
| Ebanol | 2.00 |
| Eugenol | 10.00 |
| Evernyl | 3.00 |
| Fixolid | 40.00 |
| Isoraldein 40 | 30.00 |
| Lavandin ess. | 100.00 |
| Peppermint oil | 10.00 |
| Romarin ess. | 30.00 |
| Muscatel sage oil | 30.00 |
| Thyme ess. | 10.00 |
| Total: | 1000.00 |

The compound 1 is of pronounced aromatic character, woody and camphor-like, it confers freshness and naturalness to the composition, it intensifies the notes of the agrestic type.

h) Perfume base for soap, flowery, aldehydic, woody type

| | Parts by weight |
|---|---|
| (1) | 5.00 |
| Vetivenyl acetate | 30.00 |
| Decyl acetate | 3.00 |
| Undecyl aldehyde | 4.00 |
| Lauric aldehyde | 7.00 |
| Coumarin | 60.00 |
| Dipropylene glycol | 166.00 |
| Irisanthem (3-methyl-4-(2,6,6-tri-methyl-2-cyclohexen-1-yl)-3-buten-2-one) | 170.00 |
| Jasmine reconstitution | 100.00 |
| Musk ketone | 70.00 |
| Phixia (hydroxycitronellal) | 200.00 |
| Rose reconstitution | 80.00 |
| Vanillin | 5.00 |
| Ylang ylang ess. | 100.00 |
| Total: | 1000.00 |

The compound I has a spicy green, camphor like note. It confers freshness to the composition and intensifies the woody and vetiver-like character.

i) Perfume base for soap, agrestic

|  | Parts by weight |
|---|---|
| (6) | 30.00 |
| Bornyl acetate | 100.00 |
| Vetivenyl acetate | 200.00 |
| Bergamot ess. | 100.00 |
| Citrus ess. | 100.00 |
| Dihydromyrcenol | 50.00 |
| Dipropylene glycol | 171.00 |
| Ebanol | 1.00 |
| Eugenol | 10.00 |
| Evernyl | 3.00 |
| Isoraldein 40 | 30.00 |
| Lavandin ess. | 100.00 |
| Peppermint oil | 10.00 |
| Musk ketone | 25.00 |
| Romarin ess. | 30.00 |
| Muscatel sage ess. | 30.00 |
| Thyme ess. | 10.00 |
| Total: | 1000.00 |

By virtue of its fresh, green note and its thuyon and mugwort character the compound I brings the required strength, power and freshness to the composition.

k) Perfume base for shampoos, aldehydic type

|  | Parts by weight |
|---|---|
| (9) | 10.00 |
| Cinnamaldehyde | 350.00 |
| Lauric aldehyde 10%/DIP | 5.00 |
| Aldehyde iso C11 (10%/DIP) (mixture of 10-undecenal and cis,trans 9-undecenal) | 5.00 |
| Citronellol | 60.00 |
| Coumarin | 35.00 |
| β-Dihydroionone | 10.00 |
| Dipropylene glycol | 72.00 |
| Ebanol | 1.00 |
| Fixolid | 100.00 |
| Gardenol | 7.00 |
| Geraniol | 60.00 |
| Heliotropin | 20.00 |
| Iso E super | 25.00 |
| Isoraldein 40 | 70.00 |
| Lilial | 100.00 |
| Methyl cedryl ketone | 40.00 |
| Ylang ylang ess. | 30.00 |
| Total: | 1000.00 |

The compound I has a woody, iris-like and green character, it thereby binds the woody, iris-like mild aldehydic flowery notes of the composition, further it confers volume to the composition.

l) Perfume base for shampoos, aldehydic, cosmetic

|  | Parts by weight |
|---|---|
| (4) | 2.00 |
| Hexylcinnamaldehyde | 350.00 |
| $C_{12}$-aldehyde 10%/DIP | 5.00 |
| Aldehyde iso C11 (10%/DIP) (mixture of 10-undecenal and cis,trans 9-undecenal) | 5.00 |
| Citronellol extra | 60.00 |
| Coumarin | 35.00 |
| Dipropylene glycol | 61.00 |
| Ebanol | 2.00 |
| Fixolid | 100.00 |
| Gardenol | 7.00 |
| Geraniol | 60.00 |
| Heliotropin | 20.00 |
| β-Ionone | 10.00 |
| Iso E super | 25.00 |
| Isoraldein 40 | 70.00 |
| Lilial | 100.00 |
| Methyl cedryl ketone | 40.00 |
| Ylang ylang ess. | 30.00 |
| Total: | 1000.00 |

The composition receives an overall and full character by the presence of I and, respectively, its fruity, lactone-like, woody notes.

m) Perfume base for shampoo, aldehydic

|  | Parts by weight |
|---|---|
| (3) | 80.00 |
| Hexylcinnamaldehyde | 350.00 |
| $C_{12}$-aldehyde 10%/DIP | 5.00 |
| Aldehyde iso C11 (10%/DIP) | 5.00 |
| Citronellol | 60.00 |
| Coumarin | 35.00 |
| β-Dihydroionone | 10.00 |
| Ebanol | 1.00 |
| Fixolid | 100.00 |
| Gardenol | 7.00 |
| Geraniol intermediate 60 | 60.00 |
| Givescone | 2.00 |
| Heliotropin | 20.00 |
| Iso E super | 25.00 |
| Isoraldein 40 | 70.00 |
| Lilial | 100.00 |
| Methyl cedryl ketone | 40.00 |
| Ylang ylang ess. | 30.00 |
| Total: | 1000.00 |

In this purfume, which is especially suitable for shampoos, the compound I contributes the required body and the required volume, namely on the basis of its woody and fruity note.

n) Perfume base for soap; note; flowery, reminiscent of oranges and woody

|  | Parts by weight |
|---|---|
| (11) | 5.00 |
| Benzyl acetate | 150.00 |
| Linalyl acetate | 40.00 |
| Phenyl ethyl alcohol | 50.00 |
| Ciste abs. | 1.00 |
| Coumarin | 70.00 |
| Dipropylene glycol | 300.00 |
| Estragol | 1.00 |
| Ethylvanillin 10%/DIP | 5.00 |
| Geraniol intermediate 60 | 10.00 |
| Clove leaf oil | 15.00 |
| Indolen | 1.00 |
| Ionanthem 100% | 20.00 |
| Isoeugenol | 10.00 |
| Isoraldein 70 | 65.00 |
| Lilial | 30.00 |
| Linalool | 45.00 |
| Musk xylene | 25.00 |
| Orange cryst. | 2.00 |
| Petitgrain ess. | 5.00 |
| Styrax | 15.00 |
| α-Terpineol | 30.00 |
| Vetiver ess. Java | 25.00 |
| Ylang ylang oil | 80.00 |
| Total: | 1000.00 |

In this perfume composition the green and aldehydic note of I contributes markedly to the impact; likewise I brings much green freshness into the top note of the composition.

We claim:

1. An odorant composition comprising an effective amount of a compound of the formula

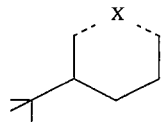

I wherein ... X .. is >CH—OR wherein R is H, COCH$_3$, COCH$_2$CH$_3$, CO—CH(CH$_3$)$_2$, CO—CH=CH$_2$, or COOCH$_3$ whereby the cis/trans ratio in the isomers of I is about 65–95:35–5.

* * * * *